(12) United States Patent (10) Patent No.: US 8,568,594 B2
Gilar et al. (45) Date of Patent: Oct. 29, 2013

(54) METHOD FOR SEPARATING PEPTIDES AND PROTEINS

(75) Inventors: Martin Gilar, Franklin, MA (US); Ying-Qing Yu, Uxbridge, MA (US); Jennifer Fournier, Milford, MA (US); John E. O'Gara, Ashland, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 13/545,762

(22) Filed: Jul. 10, 2012

(65) Prior Publication Data

US 2013/0011925 A1 Jan. 10, 2013

Related U.S. Application Data

(60) Division of application No. 11/971,256, filed on Jan. 9, 2008, now abandoned, which is a continuation-in-part of application No. PCT/US2007/061649, filed on Feb. 6, 2007.

(60) Provisional application No. 60/808,738, filed on May 26, 2006, provisional application No. 60/771,540, filed on Feb. 8, 2006.

(51) Int. Cl.
*B01D 15/08* (2006.01)

(52) U.S. Cl.
USPC ..... 210/635; 210/656; 210/198.2; 210/502.1; 530/413; 530/417

(58) Field of Classification Search
USPC ................. 210/635, 656, 659, 198.2, 502.1; 530/413, 417
See application file for complete search history.

(56) References Cited

U.S. PATENT DOCUMENTS

| | | | |
|---|---|---|---|
| 4,727,137 A | 2/1988 | Vallee et al. | |
| 4,927,541 A | 5/1990 | Matsuda et al. | |
| 5,057,426 A | 10/1991 | Henco et al. | |
| 5,223,435 A * | 6/1993 | Kohr | 436/89 |
| 5,618,438 A | 4/1997 | Fritz et al. | |
| 6,503,396 B2 * | 1/2003 | Kim et al. | 210/634 |
| 6,746,608 B2 * | 6/2004 | Smiley | 210/656 |
| 2002/0060290 A1 | 5/2002 | Pham | |
| 2004/0020857 A1 * | 2/2004 | Belew et al. | 210/660 |
| 2004/0089606 A1 * | 5/2004 | Kirkland et al. | 210/656 |
| 2004/0191516 A1 * | 9/2004 | Jiang et al. | 428/405 |
| 2005/0048553 A1 * | 3/2005 | Chenna et al. | 435/6 |
| 2005/0178730 A1 * | 8/2005 | Li | 210/656 |
| 2006/0070937 A1 * | 4/2006 | Rustamov et al. | 210/198.2 |

* cited by examiner

*Primary Examiner* — Ernest G Therkorn
(74) *Attorney, Agent, or Firm* — McCarter & English, LLP; Deborah M. Vernon; Daniel A. Wespe

(57) ABSTRACT

Embodiments of the present invention are directed to articles of manufacture, devices, methods and apparatus for performing liquid chromatography featuring a chromatographic sorbent having one or more pentafluorophenyl groups, wherein said one or more pentafluorophenyl groups are a bonded phase on a sorbent selected from the group comprising silica, organic polymers or hybrid organic silane material and said pentafluorophenyl groups are in a mono-, bi-, and tridentate forms.

21 Claims, 12 Drawing Sheets

METHOD FOR SEPARATING PEPTIDES AND PROTEINS

CROSS REFERENCE RELATED APPLICATION INFORMATION

This application is a continuation of Ser. No. 11/971,256, filed Jan. 9, 2008,which is a continuation in part of Patent Cooperation Treaty Application International application No. PCT/US2007/061649 filed Feb. 6, 2007 and U.S. Provisional Patent Application No. 60/771,540, filed Feb. 8, 2006 and 60/808,738, filed May 26, 2006. The contents of these applications are incorporated herein by reference.

FIELD OF THE INVENTION

This invention relates to devices and methods for the separation, isolation and identification of phosphorylated peptides and proteins.

BACKGROUND OF THE INVENTION

In recent years, liquid chromatography in combination with mass spectrometry (LC-MS) and in particular liquid chromatography in combination with tandem mass spectrometry (LC-MS/MS) has become a common technique for the analysis of phosphorylated proteins. Typically a protein sample is digested using a proteolic enzyme, such as trypsin. From the digest mixture, phosphopeptides are separated via liquid chromatography and then analysed via tandem mass spectrometry.

The most significant problems with the above-described method are the relative sample complexity, particularly when analysing whole cells, and the low concentrations of phosphopeptides of such samples. Without implementing specific enrichment or extraction steps, it is only possible to identify the most abundant phosphopeptides.

A successful method of phosphopeptide enrichment in the art is the use of immobilised metal ion affinity chromatography (IMAC). The IMAC technique relies upon the differing affinities of some peptides for particular metal ion complexes. Though this method does give some improvements in concentration of phosphopeptides, samples still show contamination with other peptides.

The term "peptide" as used herein, refers to a polymeric chain of two or more amino acids, each linked by an amide group represented by the formula —COONR$_a$—, where R$_a$ refers to hydrogen or any possible side-chain. A peptide may also include a number of modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes and the like.

The term "phosphopeptide" as used herein, refers to the phosphorylated form of a peptide, where a phosphate group (PO$_4$)$^{3-}$ is added to the chain at one or more of the amino acid groups, giving an increase in mass corresponding to HPO$_3$.

The term "protein" as used herein, refers to a polymeric chain of peptides. A protein may also include a number of modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes and the like.

The term "phosphoprotein" as used herein, refers to the phosphorylated form of a protein, where a phosphate group (PO$_4$)$^{2-}$ is added to the chain at one or more of the amino acid groups.

The term "glycoprotein" is used to denote a protein linked to a saccharide group and a glycopeptide is a peptide linked to a saccharide group.

The term "eluent" as used herein, refers to the mobile phase in a chromatographic separation. Such a mobile phase may be a single organic solvent, water, an aqueous ionic solution, a mixture of organic solvents, a mixture of organic solvents and water or a mixture of organic solvents and aqueous ionic solution. The makeup or concentration of an eluent may change or be changed during the course of a chromatographic separation.

The term "counterion" as used herein, refers to an ion in solution in an eluent, which may displace other ions bound to the stationary phase in a chromatographic separation.

The term "eluate" as used herein, refers to a combination of the eluent and solute exiting the stationary phase after chromatographic separation.

It is an object of the present invention to provide an improved method for the separation, isolation or enrichment of analytes from a sample solution. The separated, isolated or enriched analyte may then be stored or analysed as required.

SUMMARY OF THE INVENTION

The present invention is a method for separating a sample containing a mixture of peptides or proteins and at least one analyte comprising a phosphorylated peptide or protein, comprising the steps of;
(i) providing a mixed-mode chromatographic sorbent, a first eluent and a second eluent;
(ii) loading the sample onto mixed-mode chromatographic sorbent;
(iii) eluting from the mixed-mode chromatographic sorbent in a first mode using the first eluent to produce a first eluate;
(iv) eluting from the mixed mode chromatographic sorbent in a second mode using the second eluent to produce a second eluate; and,
(v) isolating at least one phosphorylated peptide or phosphorylated protein analyte in the first eluate or the second eluate.

As used herein, the term "mixed-mode chromatographic sorbent" refers to a sorbent capable of affecting separation of a mixture in two or more chromatographic modes. For example, one mixed-mode sorbent is a sorbent capable of both reverse-phase and ion-exchange modes. As used herein, the term "reverse phase" refers to a sorbent having hydrophobic surfaces, ligands or chemical moieties bonded or incorporated thereon such that the sorbent has affinity for non-polar molecules or parts of molecules that are non-polar. The term "ion exchange" refers to a sorbent having charged or polar surfaces, ligands or chemical moieties which interact with molecules on the basis of charge. In further embodiments, this sorbent is capable of both reverse-phase and cation-exchange modes. In further embodiments, this sorbent is capable of both reverse-phase and anion-exchange modes.

One embodiment of the present invention features a mixed-mode chromatographic sorbent having a fluorophenyl group. The fluorophenyl group is preferably a bonded phase on a sorbent such as silica, or organic polymer or hybrid organic silane material. The surface of the mixed-mode sorbent can thus be described as conforming to the formula set forth below as Formula 1.

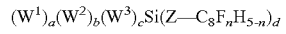   Formula 1

As used above, W$^1$, W$^2$ and W$^3$ are independently selected from the groups consisting of hydrogen, hydroxyl, hydroxyaliphatic, aliphatic, oxygen, nitrogen, and silane wherein at least one of, $W^1$, $W^2$ and $W^3$ separately represent terminal silane valences bonded to oxygen, nitrogen, carbon or silane atoms of a support, Z represents a aliphatic moiety and n is an integer from one to 5 and a+b+c+d=4; where a is 1-3; b+c is less than or equal to 2, and d is less than or equal to 3.

According to the present invention, the term "aliphatic group" includes organic moieties characterized by straight or branched-chains, typically having between 1 and 30 carbon atoms. In complex structures, the chains may be branched, bridged, or cross-linked. Aliphatic groups include alkyl groups, alkenyl groups, and alkynyl groups.

Alkyl groups include saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or cycloalkyl or alicyclic groups) (e.g., cyclopropyl, cyclopentyl, cyclohexyl, cycloheptyl, cyclooctyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups).

In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more preferably 18 or fewer. Likewise, preferred cycloalkyl groups have from 4-10 carbon atoms in their ring structure, and more preferably have 4-7 carbon atoms in the ring structure. The term "lower alkyl" refers to alkyl groups having from 1 to 6 carbons in the chain, and to cycloalkyl groups having from 3 to 6 carbons in the ring structure.

Unless the number of carbons is otherwise specified, "lower" as in "lower aliphatic," "lower alkyl," "lower alkenyl," etc. as used herein means that the moiety has at least one and less than about 8 carbon atoms. In certain embodiments, a straight-chain or branched-chain lower alkyl group has 6 or fewer carbon atoms in its backbone (e.g., $C_1$-$C_6$ for straight-chain, $C_3$-$C_8$ for branched-chain), and more preferably 4 or fewer. Likewise, preferred cycloalkyl groups have from 3-8 carbon atoms in theft ring structure, and more preferably have 5 or 6 carbons in the ring structure. The term "$C_1$-$C_6$" includes alkyl groups containing 1 to 6 carbon atoms.

Moreover, unless otherwise specified the term alkyl includes both "unsubstituted alkyls" and "substituted alkyls," the latter of which refers to alkyl moieties having substituents replacing one or more hydrogens on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamide, nitro, trifluoromethyl, cyano, azido, heterocyclyl, alkylaryl, or aromatic or heteroaromatic moieties.

An "arylalkyl" moiety is an alkyl group substituted with an aryl (e.g., phenylmethyl (i.e., benzyl)). An "alkylaryl" moiety is an aryl group substituted with an alkyl group (e.g., p-methylphenyl (i.e., p-tolyl)). The term "n-alkyl" means a straight-chain (i.e., unbranched) unsubstituted alkyl group. An "alkylene" group is a divalent moiety derived from the corresponding alkyl group. The terms "alkenyl" and "alkynyl" refer to unsaturated aliphatic groups analogous to alkyls, but which contain at least one double or triple carbon-carbon bond respectively. Suitable alkenyl and alkynyl groups include groups having 2 to about 12 carbon atoms, preferably from 1 to about 6 carbon atoms. A "vinyl" group is an ethylenyl group (i.e., —CH=CH$_2$). A "styryl" group is a vinyl-substituted phenyl group.

The term "aromatic group" includes unsaturated cyclic hydrocarbons containing one or more rings. Aryl groups can also be fused or bridged with alicyclic or heterocyclic rings which are not aromatic so as to form a polycycle (e.g., tetralin). The term "aromatic group" includes unsaturated cyclic hydrocarbons containing one or more rings. In general, the term "aryl" includes groups, including 5- and 6-membered single-ring aromatic groups that may include from zero to four heteroatoms, for example, groups derived from benzene, pyrrole, furan, thiophene, thiazole, isothiaozole, imidazole, triazole, tetrazole, pyrazole, oxazole, isooxazole, pyridine, pyrazine, pyridazine, and pyrimidine, and the like. An "arylene" group is a divalent moiety derived from an aryl group. The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms The term "amino," as used herein, refers to an unsubstituted or substituted moiety of the formula —NR$^a$R$^b$, in which R$^a$ and R$^b$ are each independently hydrogen, alkyl, aryl, or heterocyclyl, or R$^a$ and R$^b$, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. Thus, the term "alkylamino" as used herein means an alkyl group, as defined above, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The term "nitro" means —NO$_2$; the term "halogen" or "halo" designates —F, —Cl, —Br or —I; the term "thiol," "thio," or "mercapto" means SH; and the term "hydroxyl" or "hydroxyl" means —OH.

Unless otherwise specified, the chemical moieties of the compounds of the invention, including those groups discussed above, may be "substituted or unsubstituted." In some embodiments, the term "substituted" means that the moiety has substituents placed on the moiety other than hydrogen (i.e., in most cases, replacing a hydrogen) which allow the molecule to perform its intended function. Examples of substituents include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), $NO_2$, halogen (e.g., F, Cl, Br, or I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3} CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

A "substituent" as used herein may also be, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azide, heterocyclyl, aralkyl, or an aromatic or heteroaromatic moiety.

Preferably, Z is —$(CH_2)_m$— where m is 2 or 3, and more preferably 3. Preferably, n is 5 such that the fluorophenyl group is a pentafluorophenyl group.

A preferred support is silica, where the bonded phase is connected to the silica support by a siloxane (Si—O—Si) bond. The bonded phase can form a distribution of siloxane bonds with the surface of the structure of Formula 1. In the monodentate form, on one of $W^1$, $W^2$, and $W^3$ is connected by a siloxane bond to the silica support. The remaining valencies of the bonded phase can form silanol groups (Si—OH), or are bond to another nitrogen or carbon containing group that do not connect to the surface or other bonded phase groups. In the bidentate form, two of $W^1$, $W^2$, and $W^3$ form siloxane bonds with the silica surface or with other bonded phase groups. The remaining valency of the bonded phase can form silanol groups (Si—OH), or are bond to another nitrogen or carbon containing group that do not connect to the surface or other bonded phase groups. In the tridentate form, three of $W^1$, $W^2$, and $W^3$ form siloxane bonds with the silica surface or with other bonded phase groups.

Preferably, the support exhibits a distribution of monodentate, bidentate and tridentate forms. The of the surface exhibiting pentaflourophenyl groups, has 1 to 30 percent (1-30%) monodentate, 50 to 90 percent (50-90%) bidentate and 1 to 50 percent (1-50%) tridentate forms, or more preferably 2 to about 25 percent monodentate, 60 to 80 percent (60-80%) bidentate and 10 to 40 percent (10-40%) tridentate forms.

One embodiment of the present invention features a method of making the surface having the features of Formula 1. This method comprises the steps of reacting a silane surface with the compound of Formula 2 set forth:

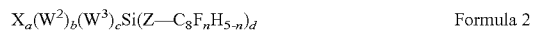
$$X_a(W^2)_b(W^3)_cSi(Z-C_8F_nH_{5-n})_d \qquad \text{Formula 2}$$

As used above X is chloride, methoxy, ethoxy, alkyl-O, alkyne-O, hydroxyl, substituted amino group, trifluoromethanesulfonate or acid group.

The mixed mode chromatographic sorbent is preferably packed in a solid phase extraction device. These devices comprise, by way of example without limitation, chromatography columns and cartridges, well devices and plates.

In one embodiment, the first eluent is a reverse-phase eluent. In one embodiment, the second eluent contains a counterion for ion-exchange. In a further embodiment, the second eluent contains a counterion for cation exchange.

Embodiments of the present invention have particular utility where the sample is a biological sample. The analyte or analytes are typically proteins or peptides, phosphoproteins or phosphopeptides. To facilitate analysis, the sample is enzymatically processed to from a protein digest, such as a tryptic protein digest.

In further embodiments, the method comprises the step of flowing the sample through an immobilised metal ion affinity capture sorbent. For example without limitation, the sorbent may comprise metal oxides such as aluminum oxide and/or titanium dioxide.

In certain embodiments, the method comprises the further step of performing liquid chromatography on at least some of first eluate or the second eluate to form a further separation product. This includes further separating at least some of the first eluate or second eluate by reverse-phase liquid chromatography to isolate proteins, peptides, phosphorylated proteins and phosphorylated peptides.

In further embodiments, at least some of the first eluate or second eluate is further analysed by secondary analysis. The secondary analysis is selected from the group consisting of ultra-violet/visual spectroscopy, fourier transform ultra violet/visual spectroscopy, infra-red spectroscopy, fourier transform infra red spectroscopy, nuclear magnetic resonance spectroscopy, fourier transform nuclear magnetic resonance spectroscopy, raman spectroscopy or evaporative light scattering detection and mass spectrometry.

A further embodiment of the present invention is directed to a chromatographic sorbent. The sorbent has one or more pentafluorophenyl groups, wherein the one or more pentafluorophenyl groups are a bonded phase on a sorbent selected from the group comprising silica, organic polymers or hybrid organic silane material. The pentafluorophenyl groups conform to the formula set forth below as Formula 1 wherein n is 5:

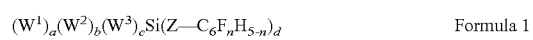
$$(W^1)_a(W^2)_b(W^3)_cSi(Z-C_6F_nH_{5-n})_d \qquad \text{Formula 1}$$

One preferred chromatographic sorbent features Z wherein Z is —$(CH_2)_m$— and m is 2 or 3.

One preferred sorbent, features a support wherein said support is silica and the terminal silane valences are bonded to silane.

Preferably, the structure of Formula 1 is distributed on the surface of the sorbent as monodentate, bidendate and tridentate forms. The distribution of monodentate, bidentate and tridentate forms, comprise 1 to 30 percent (1-30%) of the monodentate, 50 to 90 percent (50-90%) bidentate and 1 to 50 percent (1-50%) tridentate forms. Or, more preferably, the support exhibits a distribution of monodentate, bidentate and tridentate forms comprising 2 to about 25 percent of the monodentate, 60 to 80 percent (60-80%) of the bidentate and 10 to 40 percent (10-40%) tridentate forms.

Preferably, the chromatographic sorbent is held in a solid phase extraction device selected from the group consisting of columns, cartridges, well devices, and plates. And, the solid phase extraction device is part of a liquid chromatography system.

Thus, one embodiment of the present invention features a device for performing liquid chromatography comprising in a solid phase extraction device selected from the group consisting of columns, cartridges, well devices, and plates having a chromatographic sorbent having one or more pentafluorophenyl groups, wherein said one or more pentafluorophenyl groups are a bonded phase on a sorbent selected from the group comprising silica, organic polymers or hybrid organic silane material and said pentafluorophenyl groups conform to the formula set forth in Formula 1.

A further embodiment features an apparatus for separating and isolating at least one phosphorylated peptide or phosphorylated protein in a sample containing a mixture of peptides or proteins and at least one analyte comprising a phosphorylated peptide or protein analysing a sample containing at least one analyte. The apparatus has a solid phase extraction device selected from the group consisting of columns, cartridges, well devices, and plates, the solid phase extraction device having a mixed-mode chromatographic sorbent. The apparatus further comprises means for loading a sample onto said chromatographic sorbent of said solid phase extraction device; means for introducing a first eluent to said chromatographic sorbent to produce a first eluate, means for introducing a second eluent to said chromatographic sorbent to produce a second eluate, wherein at least one phosphorylated peptide or phosphorylated protein analyte in the first eluate or the second eluate.

The mixed mode chromatographic sorbent is a sorbent capable of affecting separation of a mixture in two or more chromatographic modes. In certain embodiments, this sorbent is capable of both reverse-phase and ion-exchange modes. In further embodiments, this sorbent is capable of both reverse-phase and cation-exchange modes and/or anion-exchange modes. In still further embodiments, the mixed mode chromatographic sorbent is a pentafluorophenyl sorbent having a formula as described with Formula 1.

In one embodiment, the first eluent is a reverse-phase eluent. In one embodiment the second eluent contains a counterion for ion exchange. In a further embodiment, the second eluent contains a counterion for cation exchange.

Certain embodiments further comprise a means for collecting the first eluate after separation. Embodiments may also comprise a means for collecting the second eluate after separation.

Certain embodiments further comprise a means for separation of at least some of first eluate or at least some of the second eluate. Such a means may be a chromatographic column. In some embodiments the separation means is a reverse-phase liquid chromatographic column.

Further embodiments may comprise a secondary analyser, downstream of the mixed-mode chromatographic sorbent, for analysis of at least some of the first eluate or second eluate. In certain embodiments the secondary analyser is a mass spectrometer. In other embodiments, the secondary analyser is one of an ultra-violet/visual spectroscope, fourier transform ultra violet/visual spectroscope, infra-red spectroscope, fourier transform infra red spectroscope, nuclear magnetic resonance spectroscope, fourier transform nuclear magnetic resonance spectroscope, raman spectroscope or evaporative light scattering detector.

These and other features and advantages of the present invention will be apparent to those skilled in the art upon viewing the drawings and reading the detailed description that follow.

DETAILED DESCRIPTION OF THE INVENTION

Figure 1:
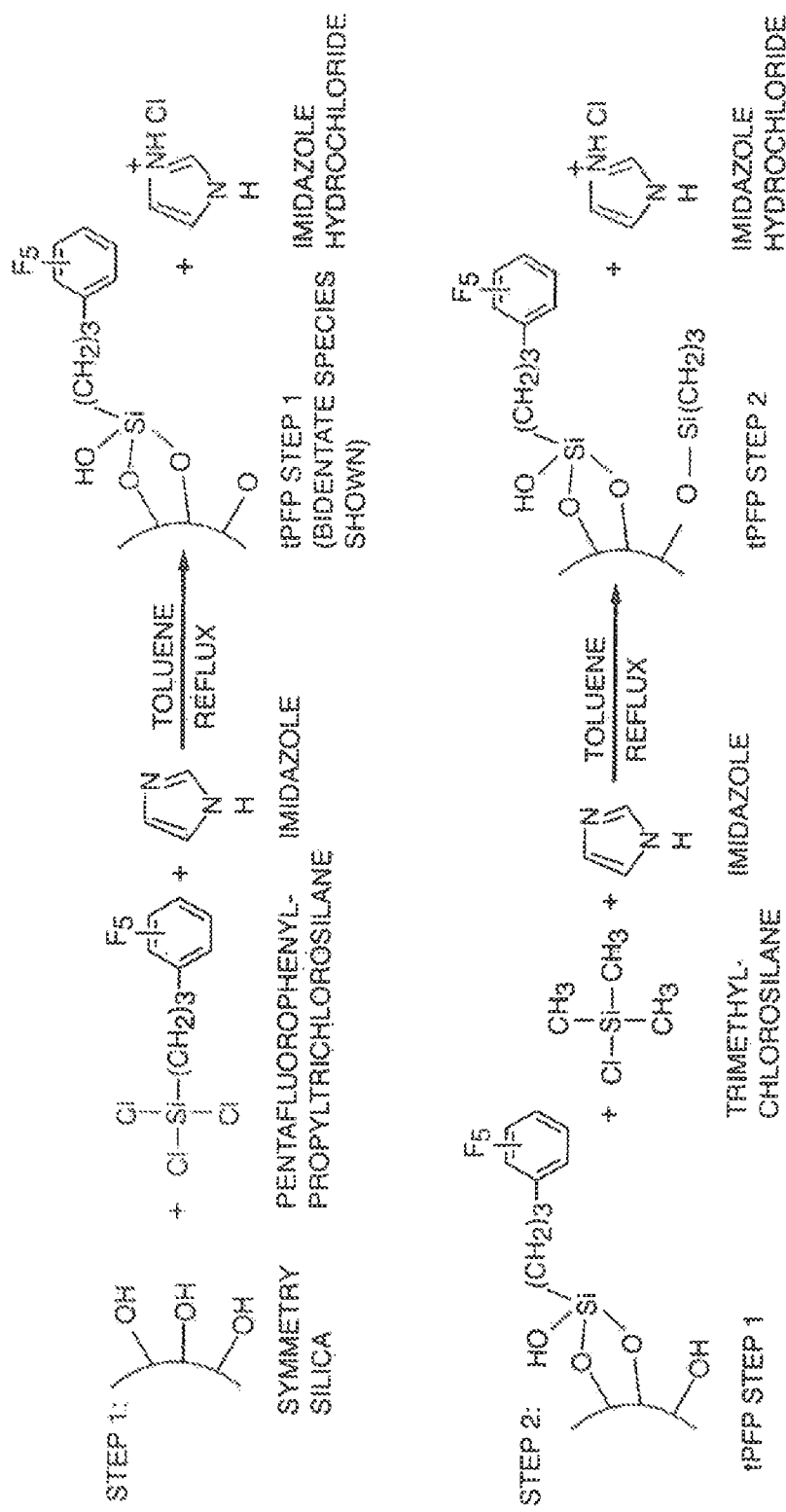
FIG. 1 depicts a schematic representation of a method of making a sorbent embodying features of the present invention.

The present invention provides apparatus, articles of manufacture, methods and systems for separating, purifying, identifying and/or analysing a compound or mixture of compounds in which one or more compounds are phosphopeptides, glycopeptides, phosphoproteins and glycoproteins. The apparatus, methods, articles of manufacture and systems of the invention are capable of separating and isolating phosphopeptides, glycopeptides, phosphoproteins and glycoproteins from complex mixtures of compounds, allowing rapid identification of components of such mixtures.

The compounds present in the mixture can be, e.g. small organic molecules (such as pharmaceuticals or candidate pharmaceuticals), peptides or polypeptides (e.g. from peptide synthesis or from biological samples, including digests of proteins or mixtures of proteins), nucleic acids or polynucleotides (e.g. from biological samples or from synthesised polynucleotides), synthetic or natural polymers, or mixtures of these materials. The types of compounds are limited only by the chromatographic methods selected for compound separation. The analytes of interest should have a separate chromatographic action in one of the modes of the sorbent to the remainder of the sample mixture. In particular, compounds may be separated by the present method and apparatus by virtue of both their charge and their hydrophobicity.

One embodiment of the present invention, directed to an article of manufacture, features a mixed-mode chromatographic sorbent having a pentafluorophenyl group. The pentafluorophenyl group is preferably a bonded phase on a sorbent such as silica, or organic polymer or hybrid organic silane material. The surface of the mixed-mode sorbent can thus be described as conforming to the formula set forth below as Formula 1.

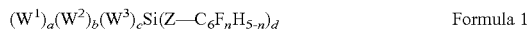

$$(W^1)_a(W^2)_b(W^3)_c\text{Si}(Z\text{—}C_6F_nH_{5-n})_d \quad \text{Formula 1}$$

As used above, $W^1$, $W^2$ and $W^3$ are independently selected from the groups consisting of hydrogen, hydroxyl, hydroxyaliphatic, aliphatic, oxygen, nitrogen, and silane wherein at least one of $W^1$, $W^2$ and $W^3$ separately represent terminal silane valences bonded to oxygen, nitrogen, carbon or silane atoms of a support, Z represents a aliphatic moiety and n is an integer from one to 5 and a+b+c+d=4; where a is 1-3; b+c is less than or equal to 2, and d is less than or equal to 3.

A preferred support is silica, where the bonded phase is connected to the silica support by a siloxane (Si—O—Si) bond. The bonded phase can form a distribution of siloxane bonds with the surface of the structure of Formula 1. In the monodentate form, on one of $W^1$, $W^2$, and $W^3$ is connected by a siloxane bond to the silica support. The remaining valencies of the bonded phase can form silanol groups (Si—OH), or are bond to another nitrogen or carbon containing group that do not connect to the surface or other bonded phase groups. In the bidentate form, two of $W^1$, $W^2$, and $W^3$ form siloxane bonds with the silica surface or with other bonded phase groups. The remaining valency of the bonded phase can form silanol groups (Si—OH), or are bond to another nitrogen or carbon containing group that do not connect to the surface or other bonded phase groups. In the tridentate form, three of $W^1$, $W^2$, and $W^3$ form siloxane bonds with the silica surface or with other bonded phase groups.

Preferably, the support exhibits a distribution of monodentate, bidentate and tridentate forms. The of the surface exhibiting pentafluorophenyl groups, has 1 to 30 percent (1-30%) monodentate, 50 to 90 percent (50-90%) bidentate and 1 to 50 percent (1-50%) tridentate forms, or more preferably 2 to about 25 percent monodentate, 60 to 80 percent (60-80%) bidentate and 10 to 40 percent (10-40%) tridentate forms.

Turning now to FIG. 1, a schematic description of the bonding of pentafluorophenyl groups on a sane support is depicted. Silica is reacted with pentafluorophenylpropyltrichlorosilane and imidazole under toluene reflux to form a bonded pentafluorophenylpropyl bonded silane. The bonded pentafluorophenyl propyl bonded silane are of the monodentate and bidendate form of which only the bidentate form is depicted.

Next, bonded pentafluorophenyl propyl bonded silane is further reacted with trimethyl chlorosilane and imidazole under toluene reflux to form pentafluorophenyl propyl bonded silane having a distribution of the monodentate, bidendate and tridentate forms.

Figure 2:
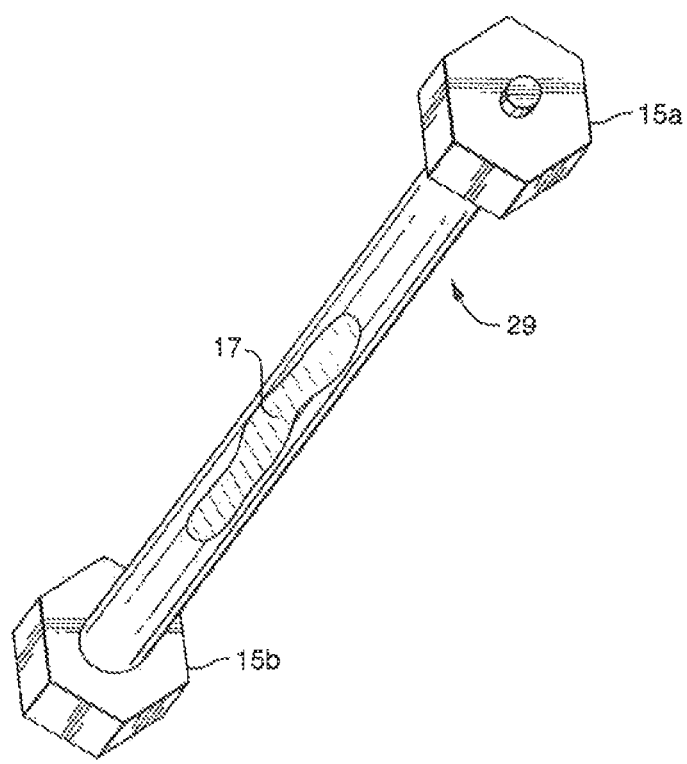
FIG. 2 depicts a device in partial cutaway embodying features of the present invention.

Turning now to FIG. 2, a device for performing separations, generally designated by the numeral 29, is depicted. Device 29 is a column having a column body 13, a fitting assemblies 15a and 15b and a sorbent 17. The fitting assemblies 15a and 15b are used to place the column 29 in fluid communication with supporting valves, pumps and detectors as will be described in later Figures. The fitting assemblies 15a and 15b are common and known in the art and the details have been simplified or omitted in FIG. 2.

The sorbent 17 is a mixed mode chromatography sorbent of the type described above, having a support with a bonded phase such as pentafluorophenyl groups. Those skilled in the art will recognise that solid phase extraction devices can take many forms of which column 29 is but one example. By way of example, without limitation, column 29 may comprise a cartridge, well device, plates, extraction tip devices and the like.

Figure 3:
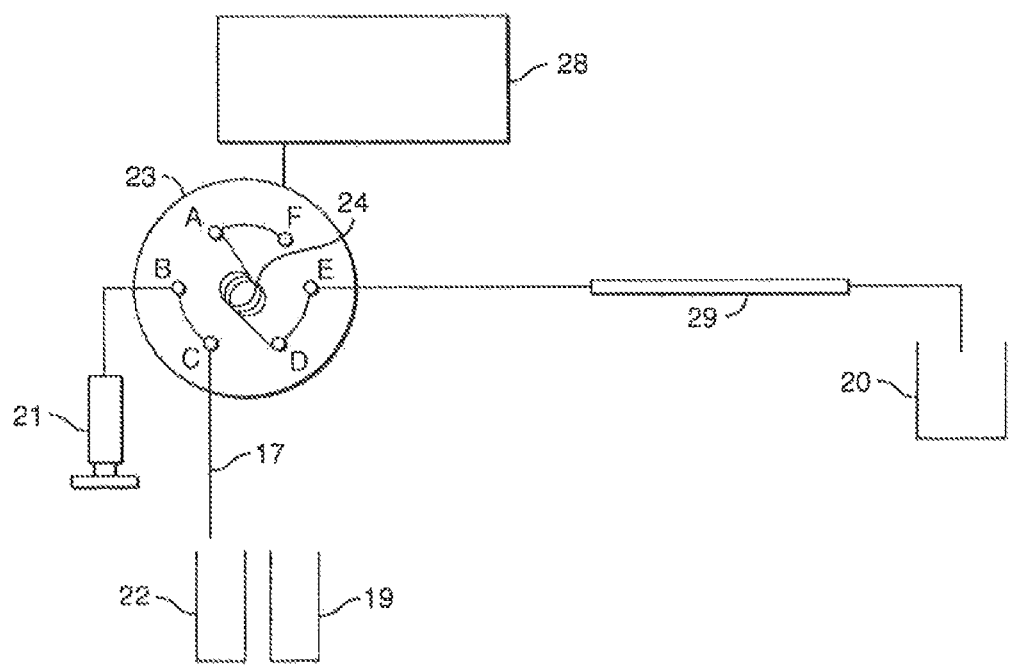
FIG. 3 depicts a schematic diagram of an apparatus embodying features of the invention.

A embodiment of an apparatus having features of the present invention is shown in FIG. 3. A multipart valve 23 has six ports, having a sample loop 24 between ports A and D, a syringe 21 at port B, a sampling needle 17 at port C, a binary gradient pump 28 at port F and a mixed mode chromatography column 29 at port E. The mixed mode chromatography column 29 is packed with a mixed mode chromatographic sorbent, capable of both reverse-phase and ion exchange modes, such as a pentafluorophenyl sorbent. Downstream of the mixed mode chromatography column 29 is a collection means 20.

Multiport valve 23 is adjusted such that ports A and B are connected and ports C and D are connected. A sample, containing at least one analyte, is drawn from sample vial 22 into sample loop 24 by syringe 21. Multiport valve 23 is then adjusted such that ports A and F and ports D and E are connected. Binary gradient pump 28 pumps a mobile phase through sample loop 24 in order to load the sample onto mixed mode chromatography column 29. Binary gradient pump then pumps a first eluent through sample loop 24 and mixed mode chromatography column 29 to produce a first eluate. The first eluent may change in composition during the elution. Such a change in composition may be, for example, an increase in organic content of the eluent in relation to aqueous content, or an increase in polar content in relation to non-polar content. In certain embodiments, the first eluent is a reverse-phase eluent. The first eluate may be collected in a collection means 20 and may contain at least one analyte.

Multiport valve 23 is further adjusted such that ports A and B are connected and ports C and D are connected. A second eluent is drawn from second eluent vial 19 into the sample loop 24 by syringe 21. The second eluent may contain a counterion for ion exchange. In certain embodiments, the second eluent may contain a counterion for cation exchange. Multiport valve 23 is then adjusted such that ports A and F and ports D and E are connected. Binary gradient pump 28 pumps the second eluent from sample loop 24 through mixed mode chromatography column 29 to produce a second eluate. The second eluate may be collected in a collection means 20 and may contain at least one analyte.

Figure 4:
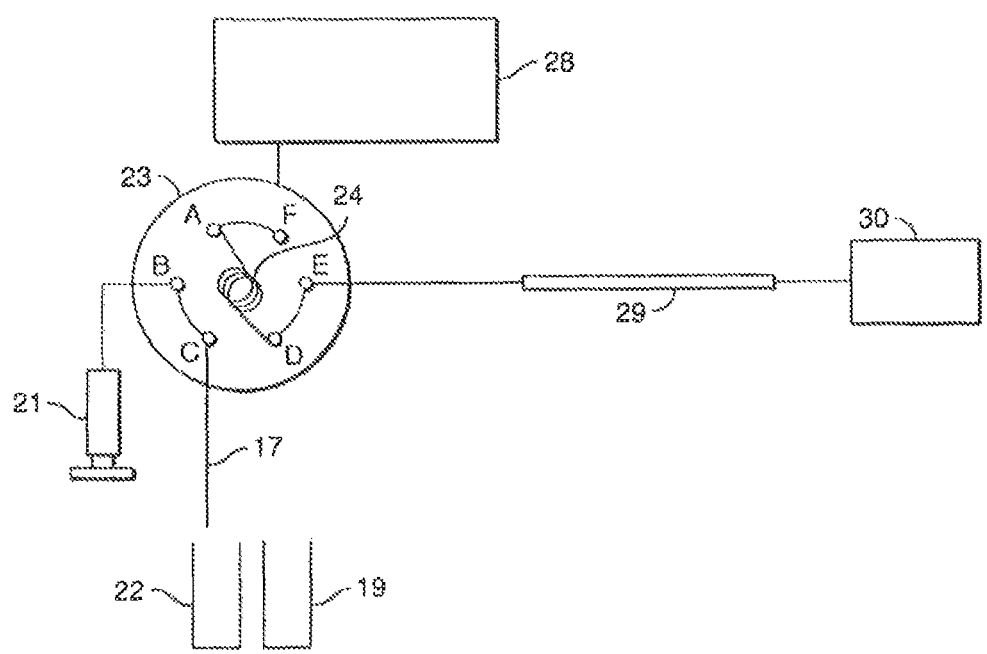
FIG. 4 depicts a schematic diagram of a second apparatus embodying features of the invention.

FIG. 4 depicts a variation in the above embodiment. A secondary analyser 30 replaces collection means 20, such that the first eluate and the second eluate may be further analysed as to their composition. Such a secondary analyser 30 may determine the structure, identity and concentration of any analytes. In one embodiment, the secondary analyser 30 is a mass spectrometer. In further embodiments, the secondary analyser may be an ultra-violet/visual spectroscope, fourier transform ultra violet/visual spectroscope, infra-red spectroscope, fourier transform infra red spectroscope, nuclear magnetic resonance spectroscope, fourier transform nuclear magnetic resonance spectroscope, raman spectroscope or evaporative light scattering detector.

Figure 5:
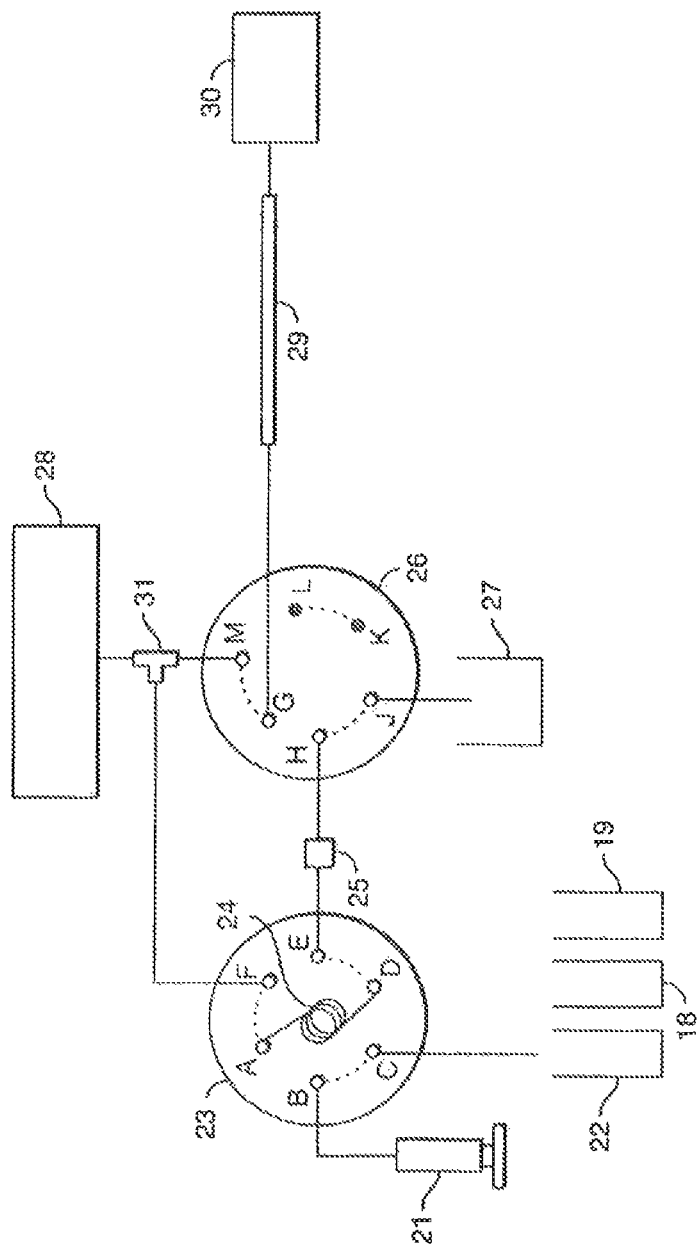
FIG. 5 depicts a schematic diagram of a third apparatus embodying features of the invention.

A further embodiment of the invention is shown in FIG. 5. A multiport valve 23 has six ports, having a sample loop 24 between ports A and D, a syringe 21 at port B, sampling needle 17 at port C, binary gradient pump 28 at port F and solid phase extraction column 25 at port F. Solid phase extraction column 25 is downstream connected to a second multiport valve at port H. In some embodiments, solid phase extraction column 25 is a titanium dioxide column. At port J is waste reservoir 27, at port M is binary gradient pump 28 (also connected to port F of first multiport valve via T-valve 31) and at port G is mixed mode chromatographic column 29. Ports L and K are closed. The mixed mode chromatography column 29 is packed with a mixed mode chromatographic sorbent, capable of both reverse-phase and on exchange modes, such as a pentafluorophenyl sorbent. Downstream of the mixed mode chromatographic column 29 is secondary analyser 30. Secondary analyser 30 may be a mass spectrometer. In other embodiments, secondary analyser 30 may be an ultra-violet/visual spectroscope, fourier transform ultra violet/visual spectroscope, infra-red spectroscope, fourier transform infra red spectroscope, nuclear magnetic resonance spectroscope, fourier transform nuclear magnetic resonance spectroscope, raman spectroscope or evaporative light scattering detector.

First multipart valve 23 is set to a position such that ports A and B are connected and ports C and D are connected. Syringe 21 then extracts sample containing at least one analyte from sample vial 22 into sample loop 24. The first multiport valve 23 is further set to a position such that ports A and F are connected and ports D and E are connected. Binary gradient pump 28 pumps a mobile phase Q through the sample loop 24, moving the sample onto solid phase extraction column 26. Mobile phase Q may be an acidic fluid, such as an aqueous organic acid. Second multiport valve 26 is set to connect ports H and J, such that excess mobile phase Q may flow to waste reservoir 27. Mobile phase Q may also flow through second multiport valve 26 and mixed mode chromatographic column 29 to a secondary analyser 30, though increased backpressure from the column makes this unfavourable.

In a further step, a mobile phase R is delivered via syringe 21 to sample loop 24. Multiport valve 23 is then positioned such that ports A and F and ports D and E are connected, such that pump 28 may transport mobile phase R to solid phase extraction column 25. Mobile phase R may be a basic fluid, such as an aqueous base. Simultaneously to the commencement of this delivery, second multiport valve 26 is positioned such that ports G and H are connected. At least a portion of the injected sample is removed from solid phase extraction column 25 and thus loaded, via the flow of mobile phase R onto mixed mode chromatographic column 29.

Pump 28 pumps a first eluent through sample loop 24 and solid phase extraction column 25 to elute a first eluate from mixed mode chromatographic column 29. The first eluent may change in composition during the elution. Such a change in composition may be, for example, an increase in organic content of the eluent in relation to aqueous content, or an increase in polar content in relation to non-polar content. In certain embodiments, the first eluent is a reverse-phase eluent.

The first eluate may be collected or transferred to secondary analyser 30 for analysis. In one embodiment, analysis is by mass spectrometry. In certain other embodiments, the analysis may be by ultra-violet/visual spectroscopy, fourier transform ultra violet/visual spectroscopy, infra-red spectroscopy, fourier transform infra red spectroscopy, nuclear magnetic resonance spectroscopy, fourier transform nuclear magnetic resonance spectroscopy, raman spectroscopy or evaporative light scattering detection.

A second eluent is delivered via syringe 21 to sample loop 24. Binary gradient pump 28 then pumps the second eluent from sample loop 24, through enrichment column 25 to elute a second eluate from mixed mode chromatographic column 29. The second eluent may contain a counterion for ion exchange. In certain embodiments the second eluent may contain a counterion for cation exchange.

The second eluate may be collected or transferred to a secondary analyser 30 for analysis. In one embodiment, analysis is by mass spectrometry. In certain other embodiments, the analysis may be by ultra-violet/visual spectroscopy, fourier transform ultra violet/visual spectroscopy, infrared spectroscopy, fourier transform infra red spectroscopy, nuclear magnetic resonance spectroscopy, fourier transform nuclear magnetic resonance spectroscopy, raman spectroscopy or evaporative light scattering detection.

Figure 6:
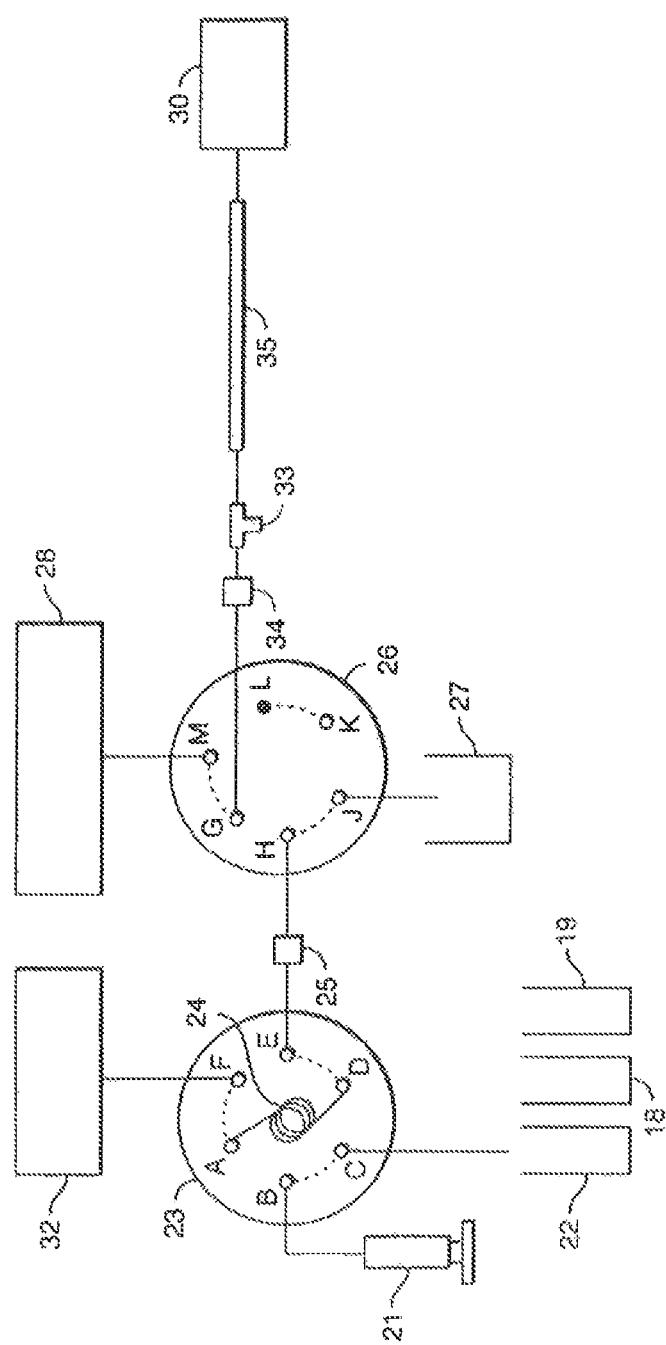
FIG. 6 depicts a schematic diagram of a third apparatus embodying features of the invention.

A further embodiment of the invention is depicted in FIG. 6. A multiport valve 23 has six ports, having a sample loop 24 between ports A and D, a syringe 21 at port B, sampling needle 17 at port C, auxiliary pump 32 at port F and solid phase extraction column 25 at port F. In some embodiments, solid phase extraction column 25 is a titanium dioxide column. Solid phase extraction column 25 is downstream connected to a second multiport valve at port H. At port J is waste reservoir 27, at port M is binary gradient pump 28 and at port G is mixed mode chromatographic trapping column 34. Mixed mode chromatographic trapping column 34 is packed with a mixed mode chromatographic sorbent, capable of both reverse-phase and ion exchange modes, such as a pentafluorophenyl sorbent. Downstream of chromatographic trapping column 34 is a T-valve 33, giving connections to port K of second multiport valve 26 and chromatography column 35. Chromatography column 35 may be capable of reverse-phase chromatography. Downstream of chromatography column 35 is secondary analyser 30. Secondary analyser 30 may be a mass spectrometer. In other embodiments, secondary analyser 30 may be an ultra-violet/visual spectroscope, fourier transform ultra violet/visual spectroscope, infra-red spectroscope, fourier transform infra red spectroscope, nuclear magnetic resonance spectroscope, fourier transform nuclear magnetic resonance spectroscope, raman spectroscope or evaporative light scattering detector.

First multiport valve 23 is set to a position such that ports A and B are connected and ports C and D are connected. Syringe 21 then extracts sample containing at least one analyte from a sample vial 22 into a sample loop 24. The first multiport valve 23 is further set to a position such that ports A and F are connected and ports D and E are connected. An auxiliary pump 32 pumps a mobile phase Q through the sample loop 24, moving the sample onto enrichment column 25. Mobile phase Q may be an acidic fluid, such as an aqueous organic acid. A second multiport valve 26 is set to connect ports H and J, such that excess mobile phase Q may flow to waste reservoir 27.

First multiport valve 23 is positioned such that ports A and B are connected and ports C and D are connected. A second mobile phase R is drawn into sample loop 24 by syringe 21. First multiport valve 23 is then positioned such that ports A and F and ports D and E are connected, such that auxiliary pump 32 may transport mobile phase R to solid phase extraction column 25. Mobile phase R is a basic fluid, such as an aqueous base. Simultaneously to the commencement of this delivery, second multiport valve 26 is positioned such that ports G and H are connected. At least a portion of the injected sample is removed from solid phase extraction column 25 and thus loaded, via the flow of mobile phase R onto mixed mode chromatographic trapping column 34. Excess mobile phase R goes to waste reservoir 26 owing to the high flow resistance of chromatography column 35.

Binary gradient pump 28 pumps a first eluent through sample loop 24 and solid phase extraction column 25 to elute a first eluate from mixed mode chromatographic sorbent 29. The first eluate may contain at least one analyte. The first eluent may change in composition during the elution. Such a change in composition may be, for example, an increase in organic content of the eluent in relation to aqueous content, or an increase in polar content in relation to non-polar content. In certain embodiments, the first eluent is a reverse-phase eluent.

The first eluate is then loaded, by means of the system pressure onto chromatography column 35. The same first eluent, a reverse-phase gradient, elutes from chromatography column 35 to further separate any multiplicity of analytes present in the first eluate.

The further separation of the first eluate is then analysed by a secondary analyser such as a mass spectrometer. In certain other embodiments, the secondary analyser may be an ultra-violet/visual spectroscope, fourier transform ultra violet/visual spectroscope, infra-red spectroscope, fourier transform infra red spectroscope, nuclear magnetic resonance spectroscope, fourier transform nuclear magnetic resonance spectroscope, raman spectroscope or evaporative light scattering detector.

First multiport valve 23 is adjusted such that ports A and B are connected and ports C and D are connected. A second eluent is drawn into sample loop 24 by syringe 21. The second eluent may contain a counterion for ion exchange. First multiport valve is then adjusted such that ports A and F and D and E are connected. Simultaneously, second multiport valve 26 is adjusted such that ports G and H are connected. Auxiliary pump 32 pumps second eluent from sample loop 24 through solid phase extraction column 25 to mixed mode chromatographic trapping column 34. When second eluent reaches mixed mode chromatographic trapping column 34, second multiport valve 26 is adjusted such that ports G and M are connected. Binary gradient pump 28 then affects the elution by the second eluent, containing at least one analyte, from mixed mode chromatographic trapping column 34 to produce a second eluate, in turn loaded onto chromatographic column 35.

Binary gradient pump 28 then pumps a further reverse-phase gradient through chromatographic column 35, further separating any multiplicity of analytes present in the second eluate.

The further separation of the second eluate is then analysed by a secondary analyser such as a mass spectrometer. In certain other embodiments, the secondary analyser may be an ultra-violet/visual spectroscope, fourier transform ultra violet/visual spectroscope, infra-red spectroscope, fourier transform infra red spectroscope, nuclear magnetic resonance spectroscope, fourier transform nuclear magnetic resonance spectroscope, raman spectroscope or evaporative light scattering detector.

Figure 7:
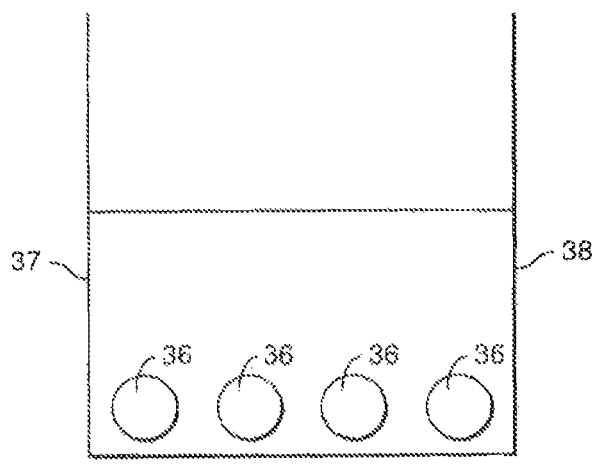
FIG. 7 depicts a schematic diagram of a third apparatus embodying features of the invention.

A further embodiment of the invention is shown in FIG. 7. Mixed-mode chromatographic beads 38 are immersed in sample 38, contained in container 37. The beads 36 are stirred to ensure effective adsorption.

Beads 36 are then removed from container 37 and washed with a first eluent, creating a first eluate. The first eluent may change in composition during the elution. Such a change in composition may be, for example, an increase in organic content of the eluent in relation to aqueous content, or an increase in polar content in relation to non-polar content. In certain embodiments, the first eluent is a reverse-phase eluent. The first eluate, which may contain at least one analyte, is collected and may be further analysed.

Beads 36 are then washed with a second eluent, creating a second eluate. The second eluent may contain a counterion for on exchange. The second eluate, which may contain at least one analyte, is collected and may be further analysed.

EXAMPLES

The present invention may be further illustrated by the following non-limiting examples describing the preparation of porous inorganic/organic hybrid materials, and their use.

Example 1

Materials

All reagents were used as received unless otherwise noted. Those skilled in the art will recognize that equivalents of the following supplies and suppliers exist, and as such the suppliers listed below are not to be construed as limiting.

Characterization

Those skilled in the art will recognize that equivalents of the following instruments and suppliers exist, and as such the instruments listed below are not to be construed as limiting.

The % C values were measured by combustion analysis (CE-440 Elemental Analyzer; Exeter Analytical Inc., North Chelmsford, Mass.). The specific surface areas (SSA), specific pore volumes (SPV) and the average pore diameters (APD) of these materials were measured using the multi-point $N_2$ sorption method (Micromeritics ASAP 2400; Micromeritics Instruments Inc., Norcross, Ga.). The SSA was calculated using the BET method, the SPV was the single point value determined for $P/P_0 > 0.98$, and the APD was calculated from the desorption leg of the isotherm using the BJH method. The micropore surface area (MSA) was determined as the cumulative adsorption pore diameter data for pores<34 Å subtracted from the specific surface area (SSA). Particle sizes were measured using a Beckman Coulter Multisizer 3 analyzer (30-µm aperture, 70,000 counts). The particle diameter (dp) was measured as the 50% cumulative diameter of the volume based particle size distribution. The width of the distribution was measured as the 90% cumulative volume diameter divided by the 10% cumulative volume diameter (denoted 90/10 ratio). Multinuclear ($^{13}C$, $^{29}Si$) CP-MAS NMR spectra were obtained using a Bruker Instruments Avance-300 spectrometer (7 mm double broadband probe). The spinning speed was typically 5.0-6.5 kHz, recycle delay was 5 sec., and the cross-polarization contact time was 6 msec. Reported $^{13}C$ and $^{29}Si$ CP-MAS NMR spectral shifts were recorded relative to tetramethylsilane using the external standards adamantine ($^{13}C$ CP-MAS NMR, □ 38.55) and hexamethylcyclotrisiloxane ($^{29}Si$ CP-MAS NMR, □ -9.62). Populations of different silicon environments were evaluated by spectral deconvolution using DMFit software. [Massiot, D.; Fayon, F.; Capron, M.; King, I.; Le Calvé, S.; Alonso, B.; Durand, J.-O.; Bujoli, B.; Gan, Z.; Hoatson, G. Magn. Reson. Chem. 2002, 40, 70-76]

Example 2

In a first step, a sample of porous, spherical 5 µm silica (Waters Corporation, 335-350 m$^2$/g) was modified with of pentafluorophenylpropyltrichlorosilane (PFP, Silar Laboratories, Wilmington, N.C.; or Gelest, Morrisville, Pa.; at 10 µmol/m$^2$ charge) using imidazole (Aldrich, Milwaukee, Wis.; at 12 µmol/m$^2$ charge) in refluxing toluene (HPLC grade, J.T. Baker, Phillipsburgh, N.J.) for 3.5 hours. The reaction was then cooled and the product was filtered and washed successively with toluene, 1:1 v/v acetone/water and acetone (all solvents from J.T. Baker). The material was then refluxed in an acetone/aqueous 0.12 M ammonium acetate solution (Sigma Chemical Co., St. Louis, Mo.) for 2 hours. The reaction was then cooled and the product was filtered and washed successively with toluene, 1:1 v/v acetone/water and acetone (all solvents from J.T. Baker). The product was then dried at 80° C. under reduced pressure for 16 hours.

In a second step, these particles were further modified with trimethylchlorosilane (Gelest Inc., Morrisville, Pa.; at 10 µmol/m$^2$ charge) using imidazole (Aldrich, Milwaukee, Wis.; at 12 µmol/m$^2$ charge) in refluxing toluene for 4 hours. The reaction was then cooled and the product was filtered and washed successively with water, toluene, 1:1 v/v acetone/water and acetone (all solvents from J.T. Baker) and then dried at 80° C. under reduced pressure for 16 hours. Important characterization data for these reactions is listed in Table 1. Surface coverage for the step 1 product was determined using the equation below.

TABLE 1

| Product | Surface Area ($m^2/g$) | Step 1 %C | PFP Surface Concentration. ($\mu mol/m^2$) | Step 2 %C |
|---|---|---|---|---|
| 1a | 341 | 9.44 | 3.33 | 10.89 |
| 1b | 341 | 9.58 | 3.39 | 10.87 |
| 1c | 350 | 9.84 | 3.42 | 11.26 |
| 1d | 350 | 10.17 | 3.58 | 11.42 |
| 1e | 335 | 9.80 | 3.56 | 11.11 |

$$\text{Surface Concentration } (\mu mol/m^2) = \frac{\%C \times 10^6}{(P_c - \%C) \times SSA \times M_{eff}}$$

where $M_{eff} = 260.25$ g/mol and $P_c = 41.39\%C$

These products were further characterized by $^{29}$Si CP/MAS NMR spectroscopy, as shown in Table 2. Recognizing the error associated with integrating $^{29}$Si CP/MAS NMR resonances, the percentage of monodentate ($T^1$) PFP ligand was found to be 15-19% for product 1c and 1d, while 1a, 1b, and 1c had lower monodentate ($T^1$) PFP populations. Degrees of condensation for the PFP bonding were determined using the calculation below, and varied between 65-76%.

TABLE 2

| Product | Relative Integration | | | Degree of Condensation |
|---|---|---|---|---|
| | $T^1$ | $T^2$ | $T^3$ | |
| 1a | 7.9 | 72.2 | 19.9 | 71% |
| 1b | 4.8 | 68.5 | 26.7 | 74% |
| 1c | 15.6 | 70.7 | 13.7 | 66% |
| 1d | 19.1 | 66.2 | 14.7 | 65% |
| 1e | 3.6 | 65.6 | 30.8 | 76% |

Degree of Condensation (%) = ($\frac{1}{3}T^1 + \frac{2}{3}T^2 + T^3$)/($T^1 + T^2 + T^3$)

Example 3

A standard reverse-phase LCMS analysis of enolase tryptic digest was performed using a Waters Alliance Bio HPLC and a Waters Micromass ZQ4000 mass spectrometer. The HPLC system was equipped with a 150×2.1 mm, 3 μm Atlantis dC18 column, and operated at 40° C. The enolate digest sample (~40 peptides) was spiked with 4 phosphopeptides (Table 1) in equimolar ratio and then loaded onto the column. The column was eluted with a reverse phase eluent, the composition and gradient of which are shown below:

Mobile phase A: 0.1% formic acid (FA) in water, pH 2.6

Mobile phase B: 0.08% formic acid in acetonitrile

Gradient: 0-50 minutes from 0 to 42% B (0.8% acetonitrile/min), 0.2 mL/min

Figure 8A:
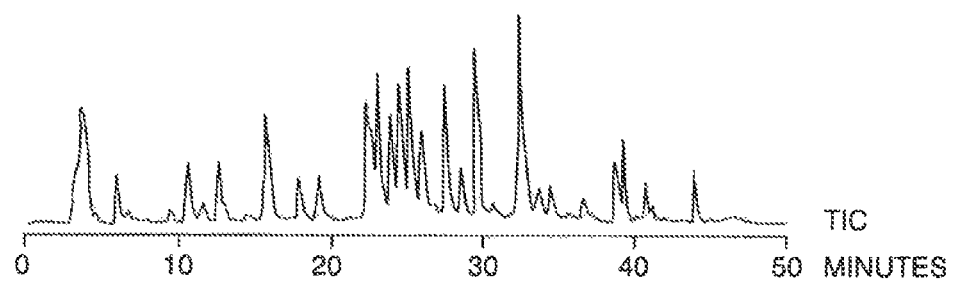
FIG. 8 depicts reverse-phase LCMS data for the analysis of enolase digest, spiked with four phosphopeptides.
Figure 8B:
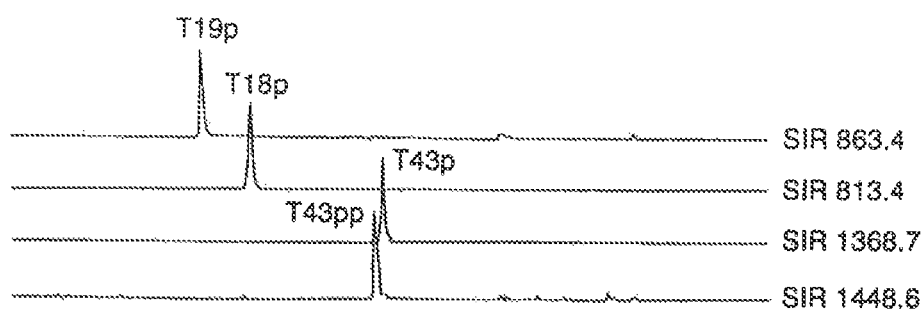

Results are shown in FIG. 8. FIG. 8A shows the raw chromatogram and FIG. 8B shows selected ion recordings (SIR) demonstrating where in the chromatogram the phosphopeptides lie.

TABLE 1

| Phosphopeptide Description | Sequence | $[M + H]^+$ | $[M + 2H]^{2+}$ |
|---|---|---|---|
| T18_1P | NVPL(pY)K | 813.38 | 407.20 |
| T19_1p | HLADL(pS)K | 863.40 | 432.21 |
| T43_1p | VNQIG(pT)LSESIK | 1368.88 | 684.84 |
| T43_2P | VNQIGTL(pS)E(pS)IK | 1448.64 | 724.83 |

In traditional RP-LC conditions all peptides are eluted without a noticeable selectivity towards phosphopeptides. Phosphopeptides are often obscured by large molar excess of non-phosphorylated peptides. Even when sample is enriched, the desirable phosphopeptides may be minor components in the mixture (enrichment methods are not 100% selective, other peptides are contaminating enriched phosphopeptides). Therefore, it is desirable to have a second enrichment step, e.g. realized by PFP column. Other advantage of off-line 2-step enrichment is that multiple fractions can be collected eluting from PFP column, hence the sample is less complex in subsequent nanoLC analysis of enriched fractions.

Example 3

An LCMS analysis, as described as the present invention, of enolase tryptic digest was performed using a Waters Alliance Bio HPLC and a Waters Micromass ZQ4000 mass spectrometer. The HPLC system was equipped with a 150×2.1 mm, 5 μm pentafluorophenyl (PFP) column, and operated at 40° C. The enolase digest sample (~40 peptides) was spiked with 4 phosphopeptides (Table 1) in equimolar ratio and then loaded onto the column. The column was first eluted with a first, reverse-phase, eluent, then a second, ion-exchange eluent. The first and second eluents were, in this instance combined into a gradient of three mobile phases, the composition and gradient of which are shown below:

Mobile phase A: 0.1% formic add in water, pH 2.6

Mobile phase B: 0.08% FA in acetonitrile

Mobile phase C: 100 mM aqueous ammonium formate, pH 3.25

Figure 9A:
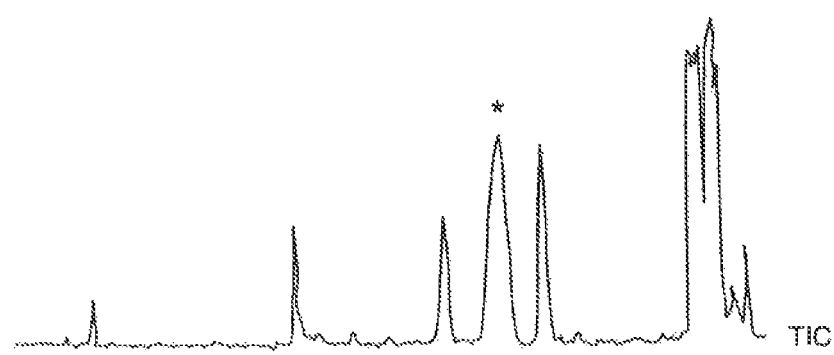
FIG. 9 depicts an analysis of an enolase digest, spiked with four phosphopeptides.

Gradient: 0-30 minutes reversed phase like gradient from 0 to 50% B, 30 to 35 ion-exchange like gradient changing 50% A to 50% C, B is kept constant at 50%; 0.2 mL/min The eluate so produced was further analysed by mass spectrometry. Results are shown in FIG. 9A.

Figure 9B:
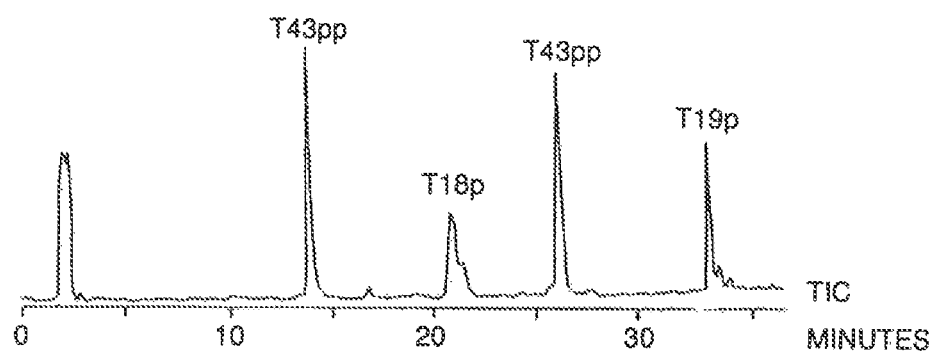

The experiment was repeated, with the sample previously treated by solid phase extraction on titanium dioxide. The results are shown in FIG. 9B FIG. 9A confirms that PFP column retains majority of tryptic peptides (enolase digest, ~40 peptides) during the first 0-30 minuets RP-like gradient, while T43pp, T18p, and T43p phosphopeptides are selectively eluted. The fourth phosphopeptide (T19p) elutes at the very beginning of ion-exchange gradient closely followed by all other enolase tryptic peptides. Peak labeled with asterisk is non-peptide system peak. FIG. 7B shows analysis of the same sample after phosphopeptide enrichment with $TiO_2$ SPE device. In this case all four phosphopeptides can be easily discerned.

Example 4

In a method for extracting glycopeptides from a sample of human serum, the sample was subjected to tryptic digestion and treated by solid phase extraction on titanium dioxide, as shown in FIG. 5. The compounds retained on the solid phase extraction device were then loaded onto the PFP column. The column was first eluted with a first, reverse-phase, eluent, and then a second, ion-exchange eluent. The reverse-phase gradient was 0-50% MeCN with 0.1% formic acid. The ion exchange eluent was 100 mM aqueous ammonium formate.

Figure 10:
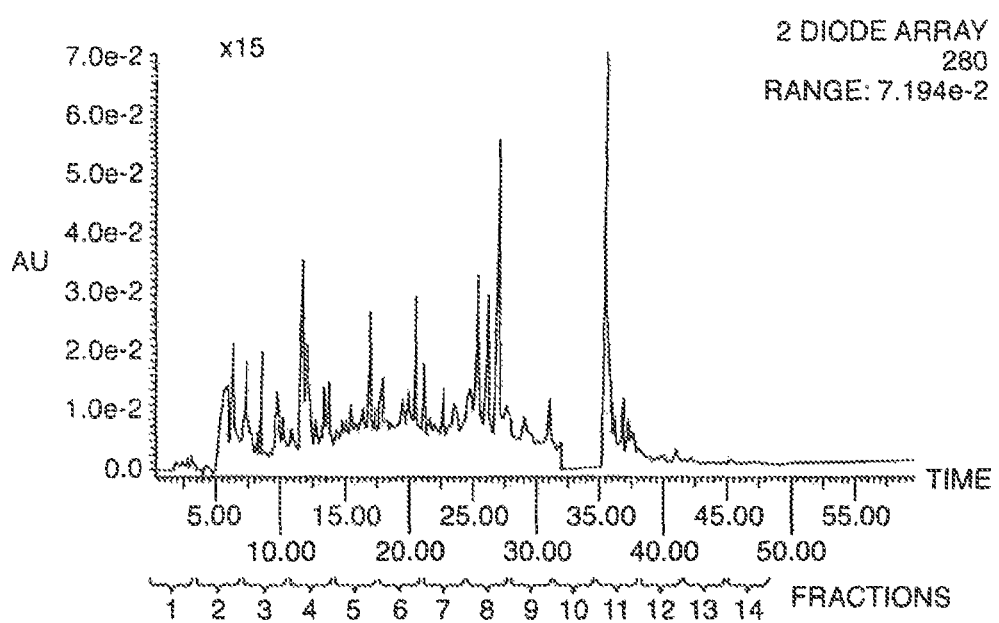
FIG. 10 depicts a UV trace of human serum.

FIG. 10 shows a UV trace of the eluate of the PFP column. Fractions 1-10 were collected under the reverse-phase gradient and fractions 11-14 under the salt gradient. UV intensities for fractions 1-10 as shown have been magnified (×15) to clearly show the sample complexity.

Figure 11:
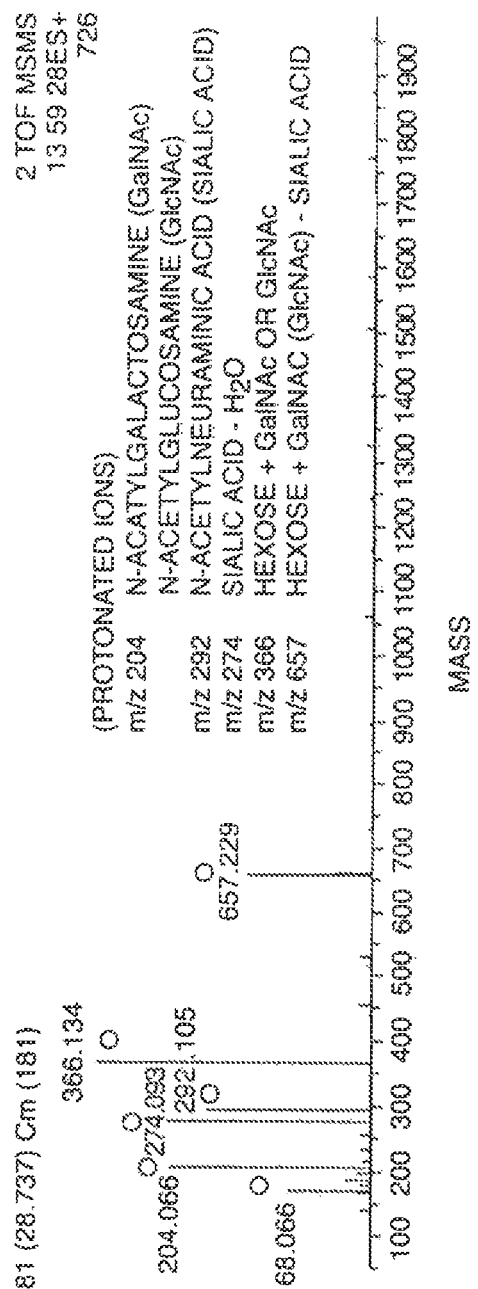
FIG. 11 depicts a LC/MS/MS fragmentation pattern for a fraction of human serum; and, FIG. 12 depicts low and high collision energy chromatograms of human serum with an ion specific chromatogram for sialic acid.

Fraction 5 was then subjected to LC/MS/MS analysis. FIG. 11 shows the typical fragmentation pattern for a sialylated glycopeptide ion contained in fraction 5. The the sorbent conforms to Formula 1:

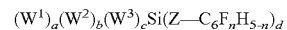

$$(W^1)_a(W^2)_b(W^3)_c\text{Si}(Z-C_6F_nH_{5-n})_d \quad \text{Formula 1}$$

where $W^1$, $W^2$, and $W^3$ are selected from the groups consisting of hydrogen, hydroxyl, hydroxy-aliphatic, aliphatic, oxygen, nitrogen, and silane wherein at least one of $W^1$, $W^2$, and $W^3$ separately represent terminal silane valences bonded to oxygen, nitrogen, carbon or silane atoms of a support, Z represents a aliphatic moiety and n is an integer from 1-5, and a+b+c+d=4; where a is 1-3; b+c is less than or equal to 2, and d is 1-3;

TABLE 2

Figure 12A:
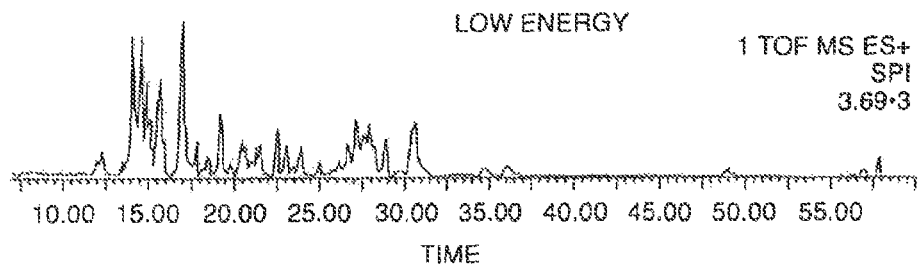
Figure 12B:
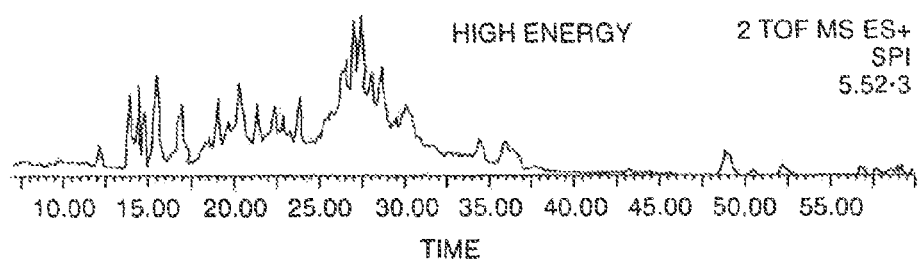
Figure 12C:
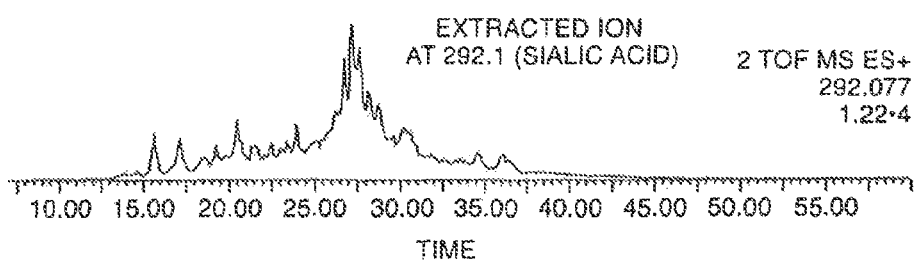

| | Fraction (4, 5, 6) | |
|---|---|---|
| Protein Name | Swissprot Accession # | |
| ITIH4_HUMAN | (Q14024) | Inter-alpha-trypsin inhibitor heavy chain H4 precursor (ITI heavy chain H4) (inter-alpha-I |
| ITIH4_HUMAN | (Q14024) | Inter-alpha-trypsin inhibitor heavy chain H4 precursor (ITI heavy chain H4) (inter-alpha-I |
| PHL1_HUMAN | (P80108) | Phosphatidylinositol-glycan-specific phospholipase D 1 precursor (EC 3.1.4.50) (PI-G PLD) |
| BTD_HUMAN | (P43251) | Blotinidase precursor (EC 3.6.1.12) |
| KAIN_HUMAN | (P29622) | Kallistatin precursor (Serpin A4) (Kallikein inhibitor) (Protease inhibitor 4) |
| ZA2G_HUMAN | (P26311) | Zinc-alpha-2-glycoprotein precursor (Zn-alpha-2-glycoprotein) (Zn-alpha-2-GP) |
| A1AG2_HUMAN | (P19652) | Alpha-1-acid glycoprotein 2 precursor (AGP 2) (Orosomucold-2) (OMD-2) |
| IBP3_HUMAN | (P17936) | Insulin-like growth factor binding protein 3 precursor (IGFBP-3) (IBP-3) (IGF-binding prot |
| CC6_HUMAN | (P13671) | Complement component C6 precursor |
| CLUS_HUMAN | (P10909) | Clusterin precursor (Complement-associated protein SP-40, 40) (Complement cytolysis inhibit |
| CO4A_HUMAN | (P0C0L4) | Complement C4-A precursor (Acidic complement C) (Contains: Complement C4 beta chain; Comp |
| CFAH_HUMAN | (P08603) | Complement factor H precursor (H factor 1) |
| CBG_HUMAN | (P08185) | Corticosteroid-binding globulin precursor (CBG) (Transcortin) |
| APOD_HUMAN | (P06090) | Apoliopoprotein D precursor (Apo-D) (ApoD) |
| HRG_HUMAN | (P04196) | Histidine-rich glycoprotein precursor (Histidine-proline-rich glycoprotein) (HPRG) |
| VINC_HUMAN | (P04004) | Vitronactin precursor (Serum spreading factor) (S-protein) (V76) [Contains: Vitronectin V6 |
| HEMO_HUMAN | (P02790) | Hemopexin precursor (Beta-1B-glycoprotein) |
| TRFE_HUMAN | (P02787) | Serotransferrin precursor (Transferrin) (Siderophilin) (Beta-1-metal binding globulin) |
| FETUA_HUMAN | (P02765) | Alpha-2-HS-glycoprotein 1 precursor (Faluin-A) (Alpha-2-Z-globulin) ( Ba-alpha-2-glycoprotein |
| A1AG1_HUMAN | (P02763) | Alpha-1-acid glycoprotein 1 precursor (AGP 1) (Orosmucoid-1) (OMD 1) |
| APOH_HUMAN | (P02749) | Beta-2-glycoprotein I precursor (Apollopoprotein H) (Apo-H) (B2GPI) (Beta(2)GPI) (Activated |
| IGHA2_HUMAN | (P01877) | Ig alpha-2 chain C region |
| MUC_HUMAN | (P01871) | Ig mu chain C region |
| IGHG4_HUMAN | (P01881) | Ig gamma-4 chain C region |
| IGHG1_HUMAN | (P01857) | Ig gamma-1 chain C region |
| IGJ_HUMAN | (P01891) | Immunoglobulin J chain |
| KNG1_HUMAN | (P01042) | Kininogen-1 precursor (Alpha-2-thiol proteinase inhibitor) [Contains: kininogen-1 heavy ch |
| AACT_HUMAN | (P01011) | Alpha-1-antichymotrypsin precursor (ACT) [Contains: Alpha-1-antichymotrypsin His-Pro-less] |
| HPTR_HUMAN | (P00739) | Haptoglobin-related protein precursor |
| CERU_HUMAN | (P00450) | Ceruloplasmin precursor (EC 1.16.3.1) (Ferroxidase) | distinguishing sialic acid peak at m/z 292.1 was used to show the presence of sialylated glycopeptides in the fraction. FIG. 12 compares the low and high collision energy chromatograms with that of an ion specific chromatogram at 292.1 sialic acid). The similarity of the high collision energy chromatogram to the chromatogram for sialic add indicates that the majority of peptides in the fraction are silylated glycopeptides.

Table 2 shows a list of glycopeptides identified from fractions 4-6 using LC/MS/MS.

Thus while preferred embodiments of the invention have been described, those skilled in the art will recognize that the present invention is subject to modification and alteration. Therefore, the invention should not be limited the precise details in the detailed description and the Figures, but should include such subject matter encompassed by the following claims and their equivalents.

The invention claimed:

1. A chromatographic method comprising the steps of:
    loading a sample potentially comprising an analyte onto a mixed-mode chromatographic sorbent, wherein the analyte comprises a modified peptide or a modified protein and wherein eluting the mixed-mode chromatographic sorbent in reverse phase mode, thereby separating the analyte, if present, from the sample; and
    eluting the mixed-mode chromatographic sorbent in ion exchange mode, thereby regenerating the mixed-mode chromatographic sorbent.

2. The method of claim 1, further comprising analyzing the analyte by LC/MS.

3. The method of claim 2, wherein the analyte eluent is substantially free of salt ions, thereby facilitating MS analysis without salt ion interference or first requiring the removal of salt ions.

4. The method of claim 1, wherein the ion exchange is cation exchange.

5. The method of claim 1, wherein the ion exchange is anion exchange.

6. The method of claim 1, wherein the analyte consists essentially of one or more phosphorylated peptides or phosphorylated proteins.

7. The method of claim 1, wherein the analyte consists essentially of one or more charged glycopeptides or glycoproteins.

8. The method of claim 1, wherein the analyte consists essentially of one or more sialylated glycopeptides or glycoproteins.

9. The method of claim 1, wherein the chromatographic sorbent comprises one or more pentafluorophenyl groups.

10. The method of claim 1, wherein the sorbent comprises a silica, organic polymer, or hybrid organic silane material and one or more pentafluorophenyl groups bonded thereto.

11. The method of claim 1, wherein Z is —$(CH_2)_m$— where m is 2 or 3.

12. The method of claim 1, wherein the support is silica where the terminal silane valences are bonded to silane.

13. The method of claim 1, wherein n is 5.

14. The method of claim 1, wherein said surface represents a distribution of the structure of Formula 1 with a distribution of monodentate, bidendate, and tridentate forms.

15. The method of claim 14, wherein the distribution comprises 1-30% monodentate form, 50-90% bidentate form, and 1-50% tridentate form.

16. The method of claim 14, wherein the distribution comprises 2-25% monodentate form, 60-80% bidentate form, and 10-40% tridentate form.

17. The method of claim 1, wherein the modified peptide or modified protein comprises a phosphorylated peptide, glycopeptide, charged glycopeptide, lapidated peptide, prenylated peptide, sulfated peptide, hydroxylated peptide, acetylated peptide, phosphorylated protein, glycoprotein, charged glyco protein, lapidated protein, prenylated protein, sulfated protein, hydroxylated protein, acetylated protein, or a combination thereof.

18. A chromatographic method comprising the steps of:
loading a sample potentially comprising an analyte onto a mixed-mode chromatographic sorbent, wherein the analyte comprises at least one modified peptide or modified protein and wherein the sorbent conforms to Formula 1:

$$(W^1)_a(W^2)_b(W^3)_c Si(Z\text{—}C_6F_nH_{5-n})_d \quad \text{Formula 1}$$

where $W^1$, $W^2$ and $W^3$ are selected from the groups consisting of hydrogen, hydroxyl, hydroxy-aliphatic, aliphatic, oxygen, nitrogen, and silane wherein at least one of, $W^1$, $W^2$, and $W^3$ separately represent terminal silane valences bonded to oxygen, nitrogen, carbon or silane atoms of a support, Z represents a aliphatic moiety and n is an integer from 1-5 and a+b+c+d=4; where a is 1-3; b+c is less than or equal to 2, and d is 1-3;

eluting the mixed-mode chromatographic sorbent in reverse phase mode, thereby separating the analyte, if present, from the sample; and eluting the mixed-mode chromatographic sorbent in cation exchange mode, thereby regenerating the mixed-mode chromatographic sorbent.

19. The method of claim 17, further comprising analyzing the analyte by LC/MS.

20. The method of claim 18, wherein the analyte eluent is substantially free of salt ions, thereby facilitating MS analysis without salt ion interference or first requiring the removal of salt ions.

21. The method of claim 18, wherein the modified peptide or modified protein comprises a phosphorylated peptide, glycopeptide, charged glycopeptide, lapidated peptide, prenylated peptide, sulfated peptide, hydroxylated peptide, acetylated peptide, phosphorylated protein, glycoprotein, charged glyco protein, lapidated protein, prenylated protein, sulfated protein, hydroxylated protein, acetylated protein, or a combination thereof.

* * * * *